United States Patent [19]

McGee

[11] 4,314,576
[45] Feb. 9, 1982

[54] UNIVERSAL SELF HELP AID APPARATUS FOR INVALIDS

[76] Inventor: Charles W. McGee, 445 Thoma St., Reno, Nev. 89502

[21] Appl. No.: 110,818

[22] Filed: Jan. 10, 1980

[51] Int. Cl.³ .................... F16M 13/08; A61H 3/04
[52] U.S. Cl. ........................................ 135/67; 297/6
[58] Field of Search ............... 135/67; 272/70.3, 70.4, 272/70; 297/5, 6; 5/81; 280/289

[56] References Cited

U.S. PATENT DOCUMENTS

| 9,215 | 8/1852 | Hopkins | 5/81 R |
|---|---|---|---|
| 503,105 | 8/1893 | Tingley | 5/81 R |
| 1,394,224 | 10/1921 | Scott | 135/67 |
| 2,759,525 | 8/1956 | Ries | 135/67 |
| 3,085,258 | 4/1963 | Wolfert | 135/67 |
| 3,249,368 | 5/1966 | Ginzburg | 297/6 |
| 3,272,530 | 9/1966 | Klassen | 297/5 |
| 3,405,954 | 10/1968 | Wolfe | 297/5 |
| 4,111,445 | 9/1978 | Haibeck | 297/5 |

OTHER PUBLICATIONS

R. H. Nyquist M.D., American Journal of Physical Medicine, vol. 41, No. 4, pp. 152-154 Aug. 1962.

Primary Examiner—Reinaldo P. Machado
Attorney, Agent, or Firm—Herbert C. Schulze

[57] ABSTRACT

This is an apparatus which has universal application for invalids who have lost much of the functioning of their limbs and other portions of their bodies such as paraplegics and the like. The apparatus is characterized by being composed of a number of tubular elements formed into a frame and having attachments of such nature that a person in a wheel chair may approach the frame and pull himself into position within the frame and with the use of various attachments about his legs and other portions of his body is able to stand, to walk and to exercise without the assistance of other persons.

8 Claims, 30 Drawing Figures

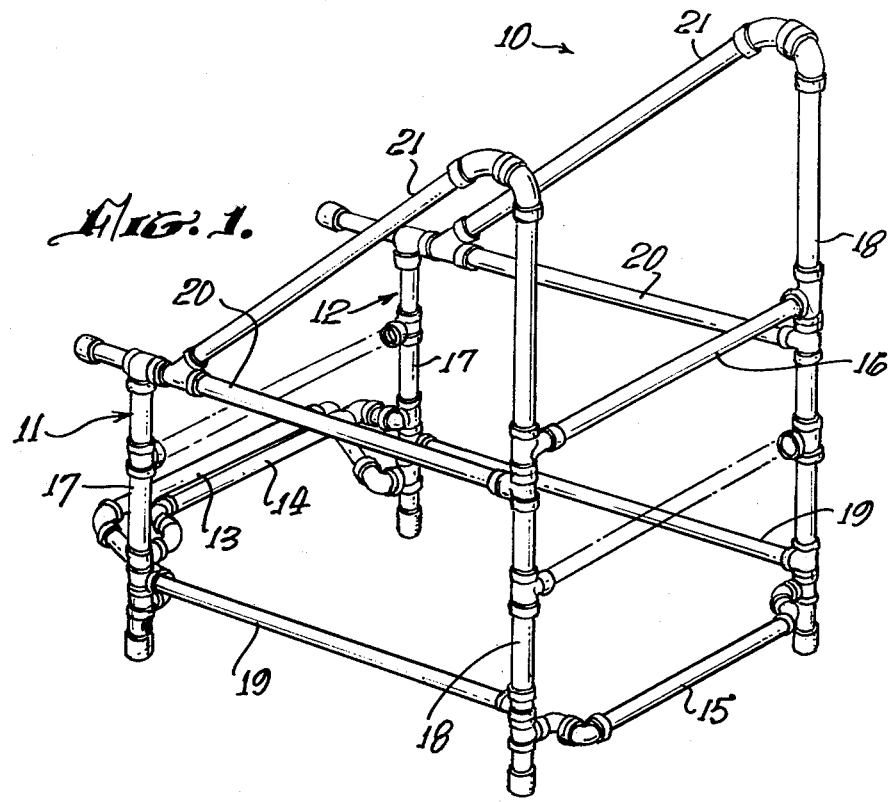
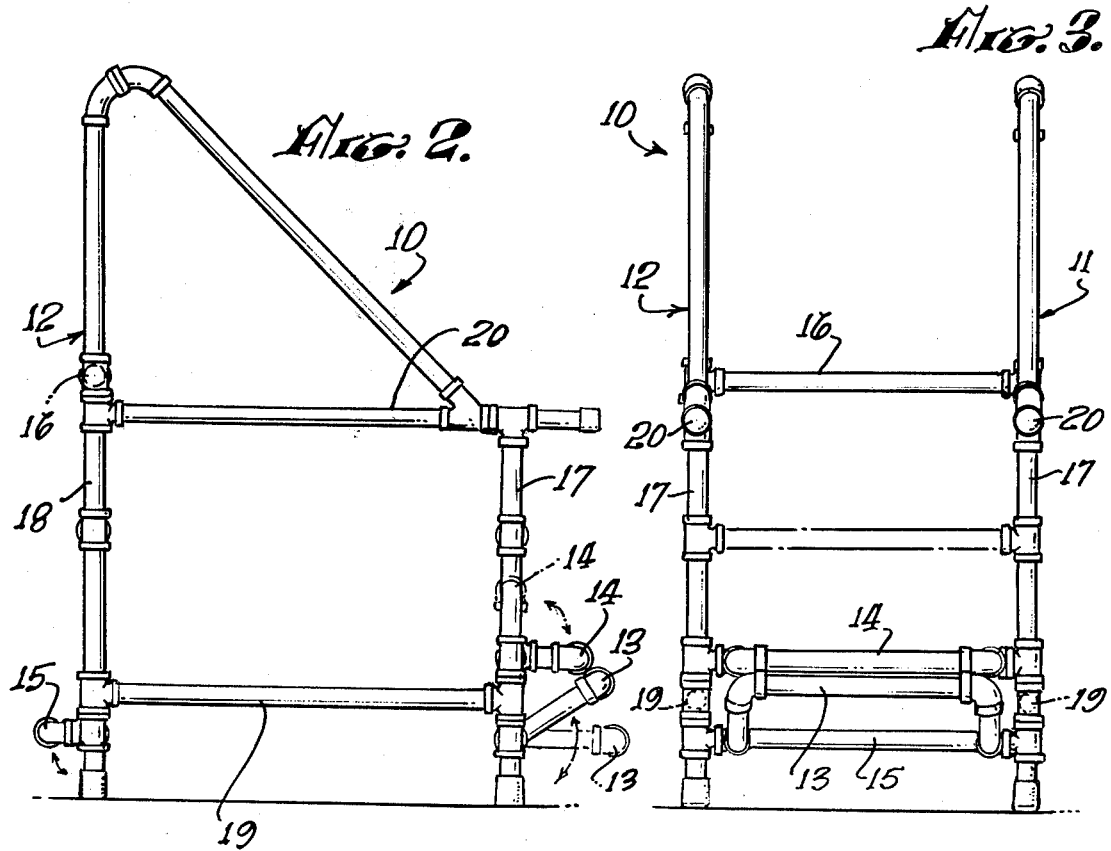

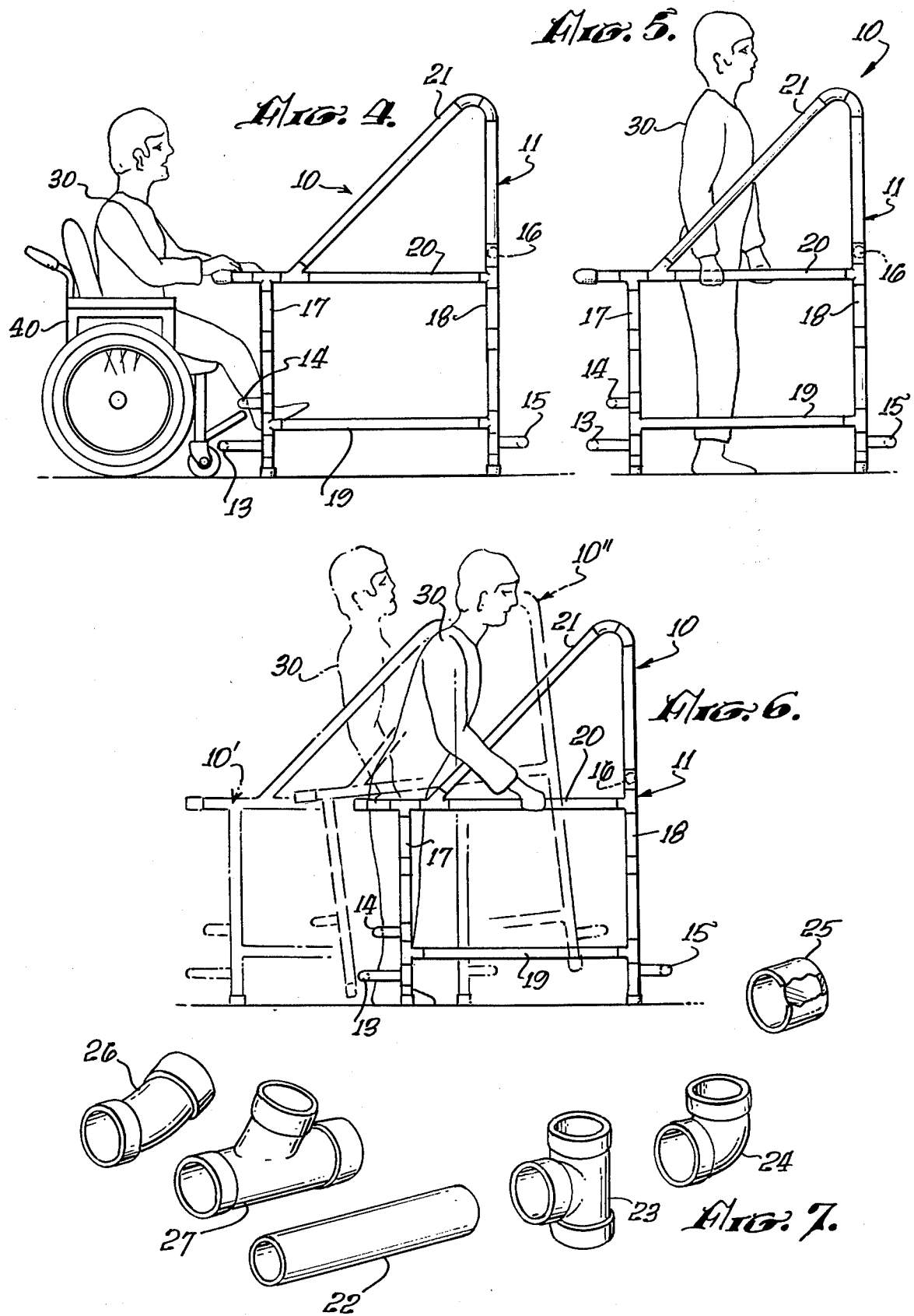

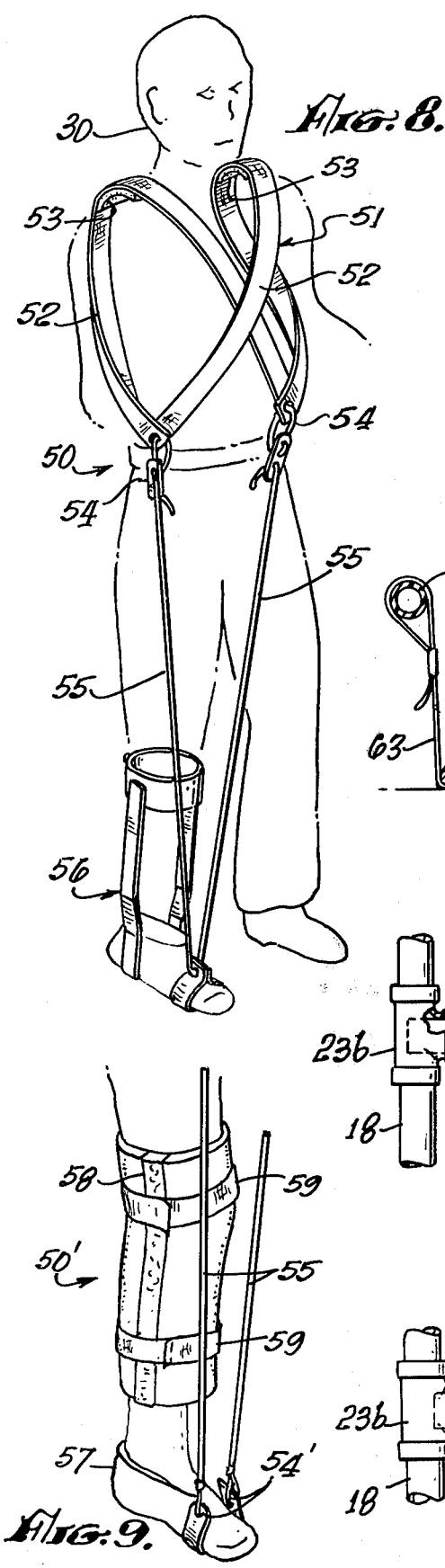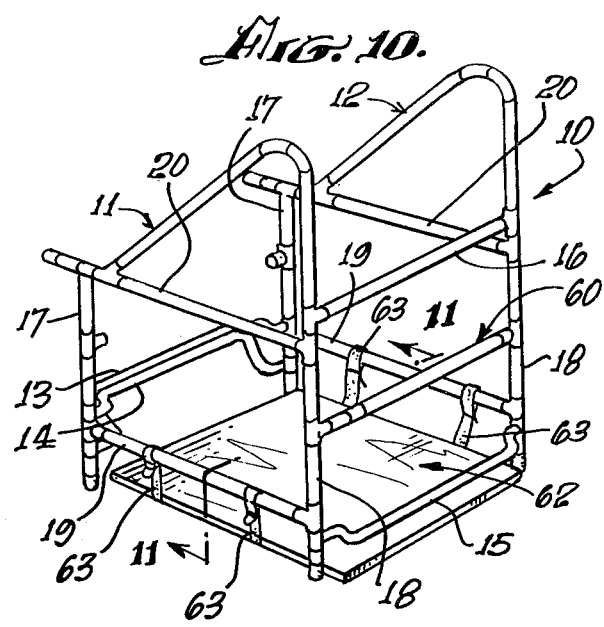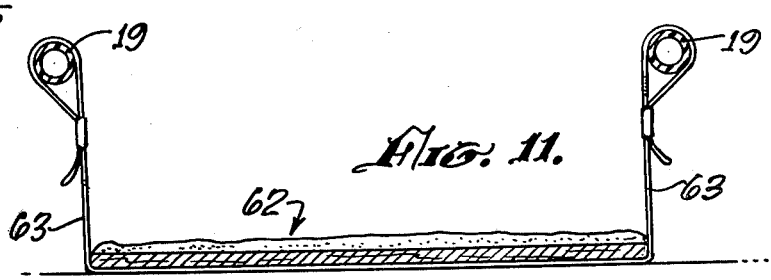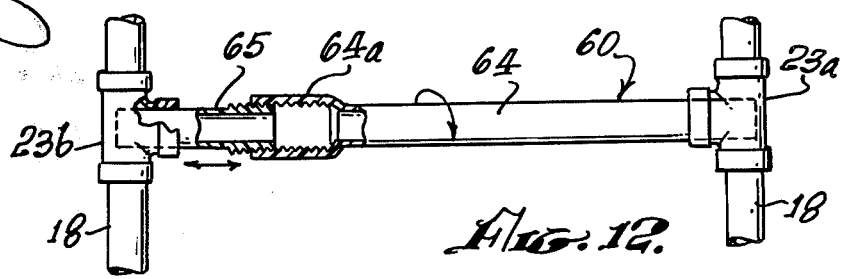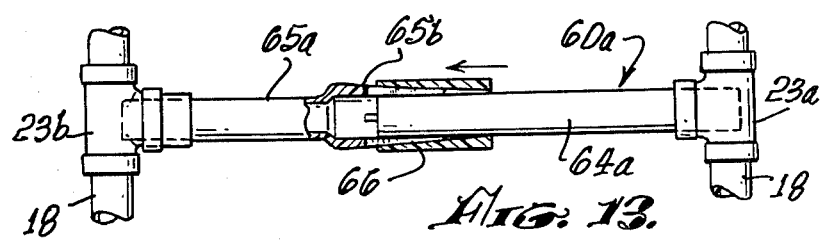

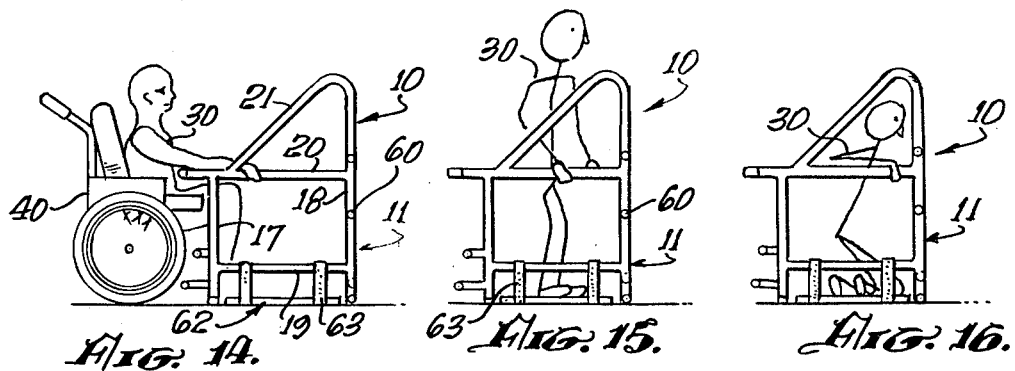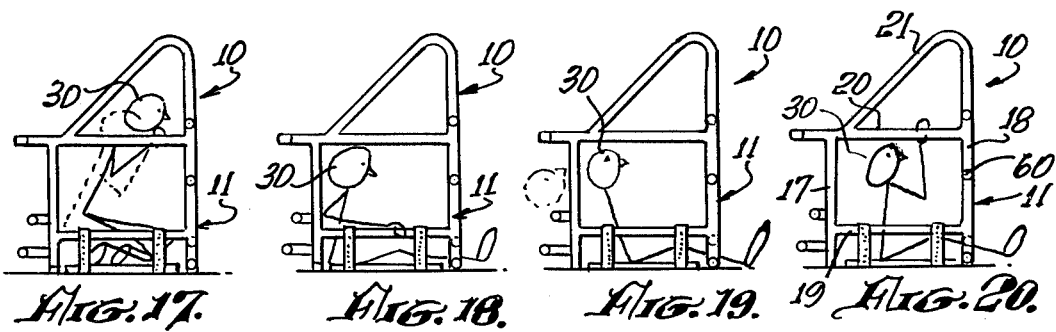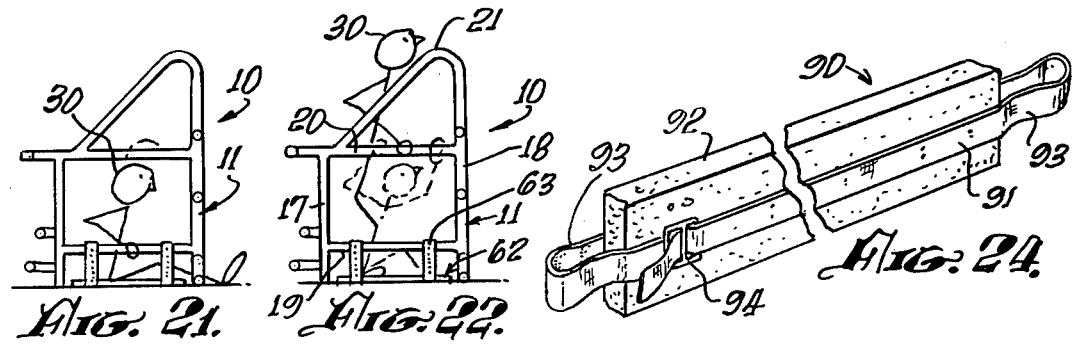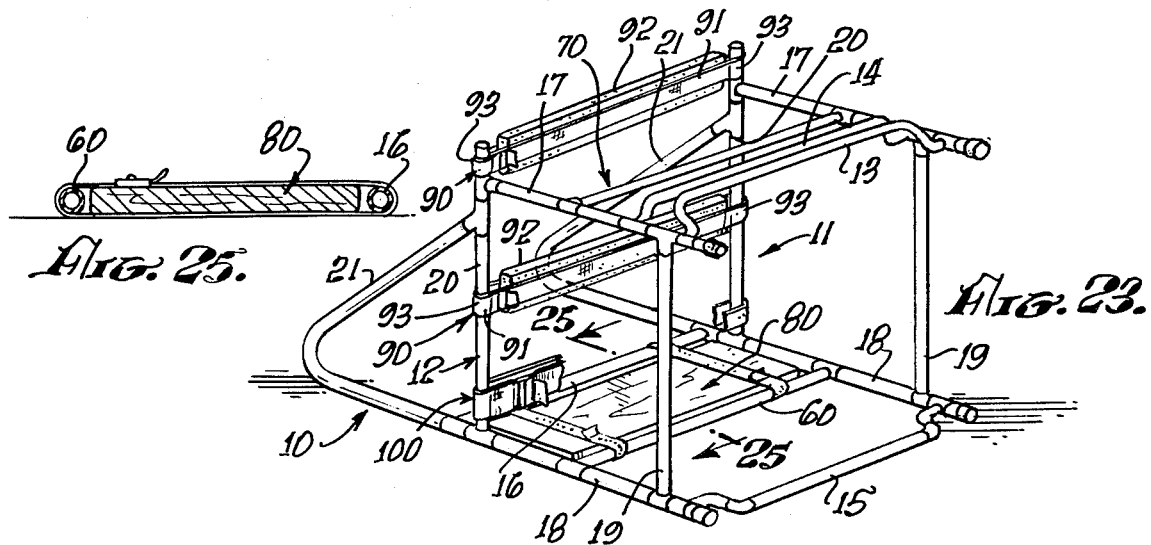

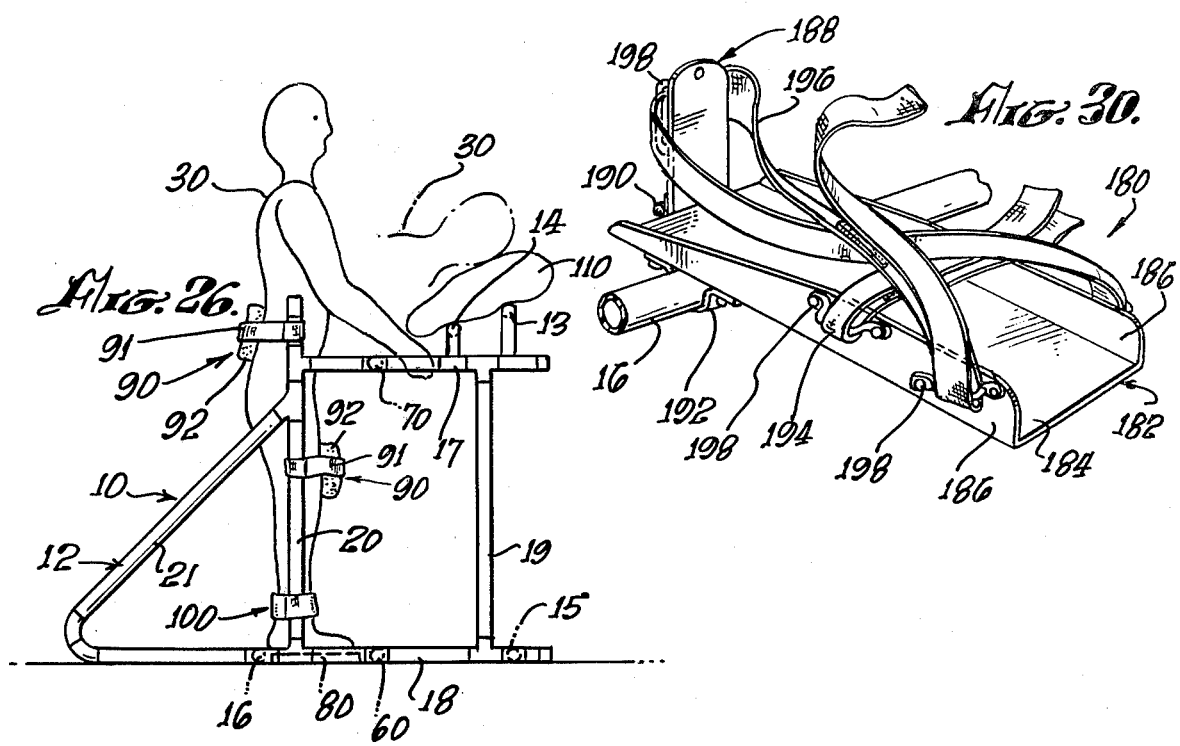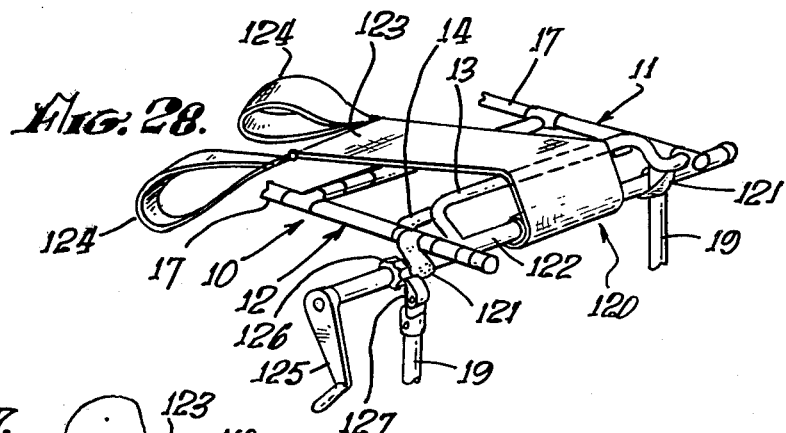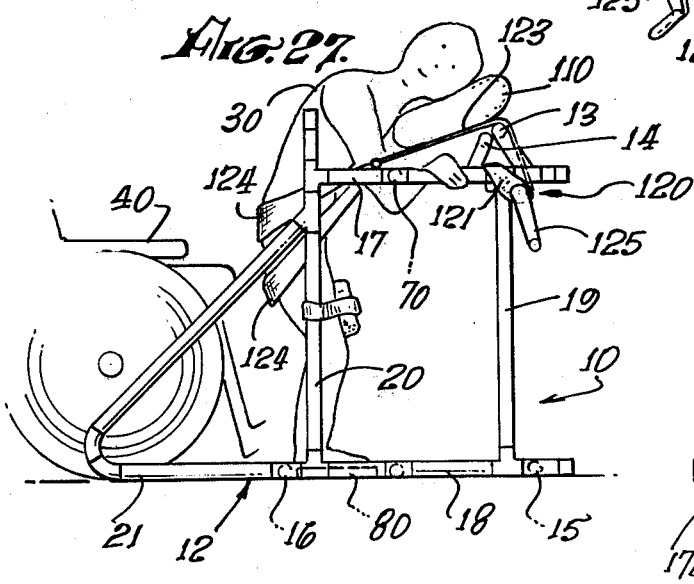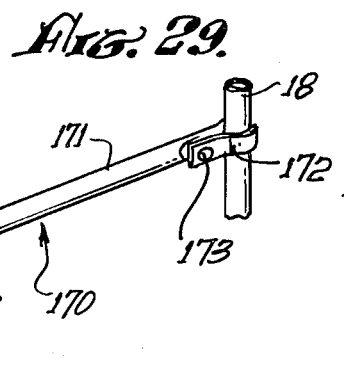

UNIVERSAL SELF HELP AID APPARATUS FOR INVALIDS

CROSS REFERENCE TO RELATED PATENT APPLICATIONS

There are no patent applications filed by me related to this application.

BACKGROUND OF THE INVENTION

1. Field of the Invention

This invention is in the general field of aids for persons suffering from loss of certain body functions, particularly the loss of use of the legs and other portions of the body. The apparatus is further and more particularly in the field of a universal self help aid in which such a crippled or invalid person may stand, walk and exercise in order to rehabilitate himself without an attendant. The apparatus is further in the field of such a device as mentioned wherein it is totally stable to prevent falling when in use and at the same time is so light in weight as to be usable with virtaully no muscle effort.

2. Description of the Prior Art

There are many devices for use by invalid or crippled persons. Such devices include exercise bars, ropes over pulleys and with handles, frames in which a person may walk and attempt to support himself, and specially constructed exercise boards, and the like. Each of such devices as previously existed helps to perform a function, but none of the devices permit a patient to approach the device in a wheel chair, assist himself into the device without danger of falling, exercise within the device and stretch and move various muscles, and ultimately allow the individual to walk, carrying the apparatus with him. Each of the prior devices, also, requires an attendant or assistant in the approach to or use of the apparatus. The present invention does not require assistance except in very unusual problem cases.

In being a universal self help aid utilized for all purposes of training and rehabilitating an invalid, there is no prior art approaching the combination of functions of this single apparatus.

Prior devices as described heretofore have not been able to be used with equal effectiveness in both the clinic or the home without special modification.

SUMMARY OF THE INVENTION

There are many persons who have become total cripples by reason of accident or otherwise wherein they are virtually unable to move any portions of their body, particularly the lower limbs. All of such persons are either bedridden or require a great deal of assistance in attempting to move their limbs and in attempting to restore some functioning to their bodies.

I have found that many persons who have been injured and left crippled as a result resent, and actually fight against, assistance from other persons in attempting to exercise. Yet, there has been no apparatus heretofore available by which such persons can safely attempt to exercise and become mobile by themselves.

Likewise, many such persons who are immobile due to injury or the like, wish to exercise and attempt to become mobile at a rate and duration of time which is not feasible due to the normal necessity of an assistant or aid of some sort in utilizing those exercise devices and the like, which are available.

I have studied this problem and have discovered there are certain brace positions for portions of the body which, if properly utilized, allow one who is otherwise unable to stand or exercise by himself to do so.

I have also found that many exercise devices are so cumbersome and heavy that they cannot be utilized and moved about by a person who has lost the use of his limbs.

Another problem which I have found is that many exercise devices are so unstable that the user is in danger of falling.

Still another problem is that such invalid persons as need exercise help as described are usually confined to wheel chairs and the exercise devices are available are not adapted to direct use by the individual without assistance from the wheel chair. Still another problem is that such invalided person whose injury is so severe that he cannot obtain a standing position himself, requires the assistance of as many as two attendants to reach such a position.

In approaching a solution to this problem, I have finally constructed a universal self help aid comprising a framework which can be approached by and departed from by a wheel chair without the necessity of assistance from another person. The framework is designed to allow the person to enter within the framework and to position his legs and other portions of the body in such manner with bracing elements as to be able to stand and exercise, manipulate, and stretch unused muscles with safety.

The device is further constructed so as to allow one person, even of less than average strength, to bring a completely disabled person to a standing position.

The device is further constructed so as to allow for freedom of the legs from the bracing elements to an extent which allows walking with the use of the framework when a patient reaches the stage of recovery where such is possible.

The entire framework has been constructed by me of tubular elements such as pipe or the like, with various fittings to join the tubular elements permanently and removably so that the apparatus can be easily transported as desired.

It is an object of this invention to provide a universal self help aid in the form of a frame-like apparatus in which a paraplegic or the like, may personally exercise without assistance.

Another object of this invention is to provide such an apparatus as described wherein the patient may walk utilizing the frame apparatus for support.

Another object of this invention is to provide an apparatus as described wherein the patient may stretch and exercise his muscles.

Another object of this invention is to provide attachments to the legs of the patient which will aid in achievement a more normal walking movement of knee and ankle.

Another object of this invention is to provide such an apparatus as is described which is light enough so that a person with very little strength may pick it up and move it while utilizing it.

Another object of this invention is to provide such an apparatus as has been described wherein the patient may exercise without danger of falling and injuring himself.

An extremely and important further object of this invention is to provide relief from muscle spasm which is customarily a problem with badly crippled individuals by reason of the ability to stretch the muscles within the device of this invention.

The foregoing and other objects and advantages of this invention will become clear to those skilled in the art upon reading the description of a preferred embodiment which follows, in conjunction with a review of the appended drawings.

BRIEF DESCRIPTION OF THE DRAWINGS

FIG. 1 is a perspective view of a preferred embodiment of the self aid device of this invention as viewed from the top, right, and rear;

FIG. 2 is a left side elevation of the device of FIG. 1;

FIG. 3 is a front elevational view of the device of FIG. 1;

FIG. 4 is a right side elevation of the device of FIG. 1 showing a patient in a wheel chair approaching the open front end of the device;

FIG. 5 is a view similar to FIG. 4 showing the patient standing in an upright position in the device;

FIG. 6 is a view similar to FIG. 5 showing the patient lifting the device from an initial phantom line position to an intermediate dotted position and finally to a solid line position practicing the "walk" mode of use;

FIG. 7 is a perspective view showing various components used in constructing the embodiment of the invention shown;

FIG. 8 is a perspective view of a harness arrangement for use in conjunction with the device shown in FIG. 1;

FIG. 9 is a perspective view showing a modification of the device of FIG. 8;

FIG. 10 is a perspective view of a modified version of the device of FIG. 1;

FIG. 11 is an enlarged sectional view taken on 11—11 of FIG. 10;

FIG. 12 is a fragmentary elevational view partly in section of a modified version of a portion of the apparatus of FIG. 10;

FIG. 13 is a fragmentary elevational view partly in section similar to FIG. 12 showing a modification;

FIGS. 14–22 are schematic views on a reduced scale of the apparatus of FIG. 10 showing numerous positions of a patient using the device as an exercising unit;

FIG. 23 is a perspective of the apparatus modified;

FIG. 24 is a perspective of a strap member used in the device of FIG. 23;

FIG. 25 is a sectional view taken on 25—25 of FIG. 23;

FIG. 26 is a side elevation showing a patient utilizing the apparatus of FIG. 23;

FIG. 27 is an elevation of the device of FIG. 23 with a patient utilizing an alternate attachment;

FIG. 28 is a perspective view of the winch attachment utilized in FIG. 27;

FIG. 29 is an alternate method of adding additional crossbars wherever needed on the apparatus of the foregoing figures; and FIG. 30 is a perspective of a further attachment that can be utilized with the exercising unit.

DESCRIPTION OF A PREFERRED EMBODIMENT

FIGS. 1 through 6 illustrate a preferred embodiment of a self aid apparatus, generally 10. The apparatus is formed of tubular members and fittings of the like, of a nature to insure good handgripping, lightness and strength while in use. The apparatus 10 is generally provided with right side assembly 11 and left side assembly 12. Crossbars 13 and 14 at the lower front connect these assemblies together and crossbars 15 and 16 complete the rectangular frame structure.

Crossbar members 13, 14 and 15 are constructed in an offset manner and are snugly mounted in frame assemblies 11 and 12 for rotation within their end fittings for purposes which will be described later in this application.

The apparatus 10 is provided with vertical front and rear posts 17 and 18, common to both right and left assemblies, horizontal lower and upper tubular members 19 and 20, and an angular tubular member 21 which connects at its upper end in a curve to vertical post 18.

FIG. 7 illustrates various tubular members and fittings used to assemble the apparatus of FIG. 1. All of these components may be of any suitable material. I have had excellent results with Schedule 40 A-B-S plastic material cemented together by A-B-S plastic cement where rotational movement is not desired. For example, the following items may be used: $1\frac{1}{2}$" diameter pipe 22, tee 23, 90° elbow 24, cap 25, 45° street elbow 26, and 45° tee 27 are representative of elements to be used. As shown in FIG. 4, a patient 30 approaches the apparatus 10 in a wheel chair 40, places his feet over the lower crossbars 13 and 14, and with the aid of his limbs lifts himself to a "standing" position indicated in FIG. 5. This is designated the "stand" mode use of the apparatus.

Having attained this position, the patient may then move forward to the rear of the space within the self aid apparatus 10 as indicated in FIG. 6 and from an original phantom line rest position of the apparatus as indicated by the referenced numeral 10' he lifts the device to the position indicated by 10" and throws the apparatus to a new rest position as shown in solid lines.

This movement enables the patient to progress forward at a pace suiting his ability. It is noted that the cross bars 13, 14 and 15 do not interfere with his feet during this "walk" mode because of being offset rearwardly and forwardly from the posts 17 and 18.

FIG. 8 shows a "walk" mode attachment 50, which helps a patient with very weak muscles in his legs and feet and who would even have difficulty in lifting one or both feet off the ground to propel himself into a forward direction.

The attachment 50 is made up of a harness 51 which is placed about the shoulders of a patient. Straps 52, provided with pads 53 are brought together at connection points 54 and provide anchor points for bungee cords 55. A solid shoe assembly 56, commonly used in therapeutic treatments is then suspended from the cords 55.

In the modification 50' of FIG. 9, the cords 55 are brought down to attachment points 54' of slipper 57 to aid a walking patient. Additionally, a pad 58 may be inserted into the open end of a removeable cast and retained by velchro band units 59 or the like, to further stiffen an otherwise flabby leg problem and help a patient to use the self aid apparatus in a "walk mode".

FIG. 10 illustrates a modification to the FIG. 1 apparatus wherein a crossbar 60 is added to the apparatus and a stabilizing board assembly 62 is employed to make the invention ready for an "exercise" mode.

FIG. 11 illustrates the stabilizing board assembly 62 in cross section having strap assemblies 63 which keep the board in place by tying it to horizontal cross members 19.

FIGS. 12 and 13 illustrate two manners in which the crossbar 60 can be placed into position on the apparatus 10. A tubular member 64 may be inserted into a tee 23a having an internally threaded end 64a which receives another externally threaded tubular member 65. As the member 65 is rotated it can move into tee 23b and fully extend the tubular member 60 for use by a patient. FIG. 13 shows a modification of member 60 which is designated 60a. In this form, tube 64a is not threaded, but moves within a second tube 65a having a tapered and split end 65b. A locking sleeve 66 then can be slipped over the junction and a chuck-like grip completes the formation of the additional bar 60a.

FIGS. 14 through 22 illustrate various exercises that can be performed by a patient. FIG. 14 shows a patient 30 approaching the apparatus 10 in a wheel chair 40. In FIG. 15, the patient has assumed a standing position with his body weight on the stabilizing board 62. In this position the ankles can be stretched.

The weight of the patient on the board anchors the apparatus 10 from movement during exercise procedures. In order to exercise the lower back and to strengthen hip and knees, the patient in FIG. 16 has lowered his body to his knees and in FIG. 17 is moving up and down as indicated in phantom lines in a manner that stretches calf muscles. By arching his back, the patient can stretch the abdomen.

In FIG. 18 the sitting position exercises lower back and abdomen muscles and FIG. 19 illustrates sit-up exercises. The added crossbar 60 is utilized in this exercise. In FIG. 20 the patient is using the self aid device for chin ups and FIG. 21 for body lifts. Finally, FIG. 22 shows the patient coming from a sitting position back up to a standing position.

It has been found that in all of the "stand", "walk" and "exercise" modes of this invention it obviously is very easy to reverse the procedure to get back into a wheel chair.

FIG. 23 illustrates a further mode of the present invention wherein the assembly 10 has been tilted and placed with its back side on the floor. The extension of the post 18 gives added stability to the apparatus. An additional crossbar 70 (similar to crossbar 60), a smaller stabilizing board 80, and a series of strap assemblies 90 and 100 have been added to the apparatus. As seen in FIGS. 24 and 25, the stabilizing board 80 is fastened to crossbars 16 and 60 by means of strap assemblies 81. FIGS. 23 and 24 illustrate strap assemblies 90 comprising bands 91 fastened to pads 92 wherein said bands form loops 93, tightened by buckle 94. These strap assemblies are shown in FIG. 23 to be mounted at the top and intermediate positions between cross members 20. At the very bottom of the posts 20 is placed a strap assembly 100 which will later be shown to encircle the ankles of the patient. In the position in which the apparatus rests on the floor as viewed in FIG. 23, the lower crossbar 15 is rotated to the indicated position in order to allow the posts 18 to be flat on the floor.

The added crossbar 70 which in essence is identical to the previously described crossbar 60 is placed between tubular members 17 at an intermediate location. As shown in FIG. 26, a patient has entered the confines of the "stall bar" mode of the self aid device 10. This is accomplished by first standing upright and placing the ankles within the strap assembly 100, and, secondly pushing forward against the intermediate strap assembly 90 which has been mounted in position and finally slipping the topmost strap assembly 90 over the extension stubs of tubular members 20. Now the patient can stand by himself in this position and do mild exercises. In addition a pillow 110 can be placed on the crossbars 13 and 14. Thus the patient can bend forward and not be without support in the position shown in phantom lines of FIG. 26.

For patients who need more help to attain an upright stature, a winch device designated generally as 120 in FIGS. 27 and 28 is provided to add onto the apparatus 10. Straps 121 affix a winch shaft 122 to the tubular members 19 and posts 17. A flat band 123 made of canvas or other woven material is fastened to the shaft in any conventional manner and has loop extensions 124 at the free end (as shown in FIG. 28). These loops can be put around upper leg portions of the patient and by rotating crank arm 125 of the winch shaft, the patient can be aided to a position indicated in FIG. 27. Also ratchet 126 and ratchet pawl 127 can be mounted onto shaft 122 and tubular member 19 in a manner known in the art to prevent the band 123 and the patient from falling back until said ratchet and pawl are manually reversed to effect such a release.

During the use of the self aid device in FIGS. 26 and 27 conditions, the patient stands on the stabilizing board 80 in order to keep the apparatus 10 firmly on the ground. The added crossbar 70 in the "stall bar" mode provides a support for the winch band 123 at its rearward end and also a bridge for the body of the patient to rest upon. Crossbars 13 and 14 can be brought together as viewed in FIG. 27 to present a sturdy crossbar for the flat band 123. In addition, a pillow 110 can be placed on the band 123 for the patient's comfort.

In FIG. 29, I have shown an additional method of adding crossbars to the apparatus 10 wherever needed. The reference character 170 shows generally the bar assembly comprising bar member 171 with clamping members 172 provided with tightening means such as bolts 173 at each end. This enables a quickly attachable and detachable means of adding bars to the apparatus.

FIG. 30 illustrates a device which can easily be placed on a foot by the patient himself which will aid in motivating the patient's ankle. This device, indicated generally by the reference numeral 180, has a foot plate 182 comprising a base 184 and sides 186. A hinged heel plate 188 hinged at 190 is rotatably mounted onto the crossbar 16 by means of bracket assembly 192. Velchro fastened strap assemblies 194 and 196 are easily wrapped around a patient's foot and ankle by looping through affixed "U" units 198. The device 180 allows a patient to exercise his ankle while in a "stand" mode.

While the embodiments of this invention shown and described are fully capable of achieving the objects and advantages desired, it is to be understood that such embodiments are for the purposes of illustration only and not for the purposes of limitation.

I claim:

1. Apparatus for assisting a crippled individual in movement and exercise comprising: a frame consisting of two side frame members, wherein said side frame members include angularly disposed members to be gripped by an individual using the device; elongated members joining said two side frame members at one of their ends include members suitable to engage the lower legs of the person using the same in a clamping manner; elongated members joining the other end of said side frame members in such a manner as to allow for entry from that end from a wheeelchair.

2. The apparatus of claim 1 wherein a foot brace is removably connected between the members which are suitable to engage the lower legs and said foot brace has attached thereto a harness suitable to be fastened onto the body of the user of the apparatus.

3. Apparatus for assisting a crippled individual in movement and exercise comprising: a frame consisting of two side frame members, wherein said side frame members include angularly disposed members to be gripped by an individual using the device; rotatably mounted elongated members joining two side frame members upon one end thereof, said rotatably mounted elongated members being offset outwardly from the frame in order to allow for movement of said crippled individual within the confines of said frame to exceed the general space provided within said frame; and rotatably mounted elongated members joining the other end of said side frame members in such a manner as to allow for entry from that end from a wheelchair.

4. The apparatus of claim 3 wherein an elongated member joining the side members of said frame at the end opposite the entry end is offset outwardly from said frame to allow movement of said crippled individual within the confines of said frame to exceed the general space provided within said frame.

5. The apparatus of claim 4 wherein an anchoring plate means is affixed to said frame by fastening means when said frame is rotated 90° from it's initial position which assisted an individual in movement and standing to a position to assist said individual to exercise upon said anchoring plate means and by assisting himself on said frame means and elongated connecting members.

6. The apparatus of claim 4 wherein said two side frames, said elongated members and said angularly disposed members to be gripped by said individual are made from 1½ diameter tubing and from a Schedule 40 A-B-S plastic material cemented together by A-B-S plastic cement where rotational movement is not desired.

7. The apparatus of claim 5 wherein a lift mechanism is attached to said frame and said lift mechanism has a harness means for supporting said individual in an upright position when said individual is a paraplegic or a quadraplegic.

8. The apparatus of claim 7 wherein said lift mechanism is a winch mechanism and said harness means includes a conveyor belt means which is supported on said elongated members and said conveyor belt means having said harness means for supporting said crippled individual.

* * * * *